United States Patent [19]
Berlioz et al.

[11] Patent Number: 5,925,565
[45] Date of Patent: Jul. 20, 1999

[54] INTERNAL RIBOSOME ENTRY SITE, VECTOR CONTAINING IT AND THERAPEUTIC USE

[75] Inventors: Clarisse Berlioz, Paris; Sandrine Jacquemoud, Lyons; Christophe Torrent, Paris; Jean-Luc Darlix, Chaponost, all of France

[73] Assignee: Institut National de la Sante et de la Recherche Medicale, Paris, France

[21] Appl. No.: 08/600,999

[22] PCT Filed: Jul. 5, 1995

[86] PCT No.: PCT/FR95/00894

§ 371 Date: Mar. 5, 1996

§ 102(e) Date: Mar. 5, 1996

[87] PCT Pub. No.: WO96/01324

PCT Pub. Date: Jan. 18, 1996

[30] Foreign Application Priority Data

Jul. 5, 1994 [FR] France ................................... 94 08300

[51] Int. Cl.$^6$ .................................................. C12N 15/00
[52] U.S. Cl. ...................... 435/325; 424/93.21; 435/455; 435/320.1; 435/69.1; 514/44; 536/23.1; 536/24.1
[58] Field of Search ...................... 424/93.21; 435/172.3, 435/320.1, 455, 69.1; 536/23.1, 24.1; 514/44

[56] References Cited

U.S. PATENT DOCUMENTS 5,354,674  10/1994  Hodgson ............................. 435/172.3

FOREIGN PATENT DOCUMENTS

| WO-A 9207950 | 5/1992 | WIPO . |
|---|---|---|
| WO-A- 9303143 | 2/1993 | WIPO . |

OTHER PUBLICATIONS

C. Bordignon et al, "Gene Therapy in Peripheral Blood Lymphocytes and Bone Marrow for ADA$^-$ Immunodeficient Patients", *Science* (1995) 270:470–475.
R. Michael Blaese et al., "T Lymphocyte–Directed Gene Therapy for ADA$^-$ SCID: Initial Trial Results After 4 Years", *Science* (1995) 270:475–480.
G. Nabel et al, "Immune Response in Human Melanoma After Transfer of an Allogeneic Class I Major Histocompatibility Complex Gene with DNA–Liposome Complexes", *Proc. Natl. Acad. Sci USA*, (1996) 93:15388–15393.
J. Pelletier et al. "Cap–Independent Translation of Poliovirus mRNA is Conferred by Sequence Elements within the 5' Noncoding Region", *Molecular and Cellular Biology*, (1988) 8:1103–1112, No. 3.
"A small and efficient dimerization/packaging signal of rat VL30 RNA and its use in murine leukemia virus–VL30–derived vectors for gene transfer", Journal of Virology, vol. 68, No. 2, pp. 661–667, Torrent, C. et al.
"Analytical study of rat retrotransponson VL30 RNA dimerization in vitro and packaging in murine leukemia virus", Journal of Molecular Biology 240 (5). 1994. 434–444. Torrent, C. et al.
"Nucleotide sequence of mouse virus–like (VL30) retrotransposon BVL–1", Nucleic Acids Research, vol. 18, No. 3, Oxford GB, p. 673, Hodgson, C. et al.
"Complete nucleotide sequence of a mouse VL30 retro–element", Molecular and Cellular Biology, vol. 8, No. 8, Washington US, pp. 2989–2998, Adams S. et al.
"New generation of safe, efficient retroviral vectors and packaging cell lines for application in gene therapy trials", Keystone Symposium on Gene Therapy and Molecular Medicine, Steamboat Springs, Colorado, USA, Mar. 26–Apr. 1, 1995. Journal of Cellular Biochemistry Supplement 0 (21A). 1995. 408, Homann, H. et al.
"Expression of VL30 vectors in primary cell types which are targets for gene therapy", Keystone Symposium on Gene Therapy and Molecular Medicine, Steamboat Springs, Colorado, USA, Mar. 26–Apr. 1, 1995. Journal of Cellular Biochemistry Supplement 0 (21A). 1995. 408, Hodgson, C. et al.
Kappel et al (1992). Current Opinion: Biotechnology 3, 548–553.
Orkin and Motulsky, (1995). Report and Recommendations of the Panel to Assess the NIH Investment: Research on Gene Therapy.
Mulligan, R. (1993). Science 260, 926–932.
Jolly, D. (1994). Cancer Gene Therapy 1 , 51–64.
Adams, S et al (1988). Molecular and Cellular Biology 8, 2989–98.
Morgan, R. et al (1992). Nucleic Acids Res. 20, 1293–1299.
Lewin, R. (1987). Science 237, 1570.
Reeck et al (1987). Cell 50, 667.
Cook, R. et al (1991). Biotechnology 9, 748–51.
Chakraborty, A et al (1993). FASEB Journal 7, 971–7.
Makris, A. et al (1993). J. Virol. 67, 1286–1291.
Torrent, C. et al (1992). Bone Marrow Transpl. 9 (Supp. 1), 143–147.
Adam, M et al (1991). J. Virol. 65, 4985–4990.
Ghattas, I. et al (1991). Mol. Cell. Biol. 11, 5848–5859.
Berlioz et al (1995). Journal of Virology 69, 2214–22.

*Primary Examiner*—Bruce R. Campell
*Assistant Examiner*—Dave Trong Nguyen
*Attorney, Agent, or Firm*—Burns, Doane, Swecker & Mathis, L.L.P.

[57] ABSTRACT

A novel internal ribosome entry cite and a novel region for the encapsidation of a retrotransposon and murine VL30s in particular are disclosed. A vector and a eukaryotic cell containing said cite and region, and their therapeutical or prophylactic use are also disclosed.

20 Claims, 4 Drawing Sheets

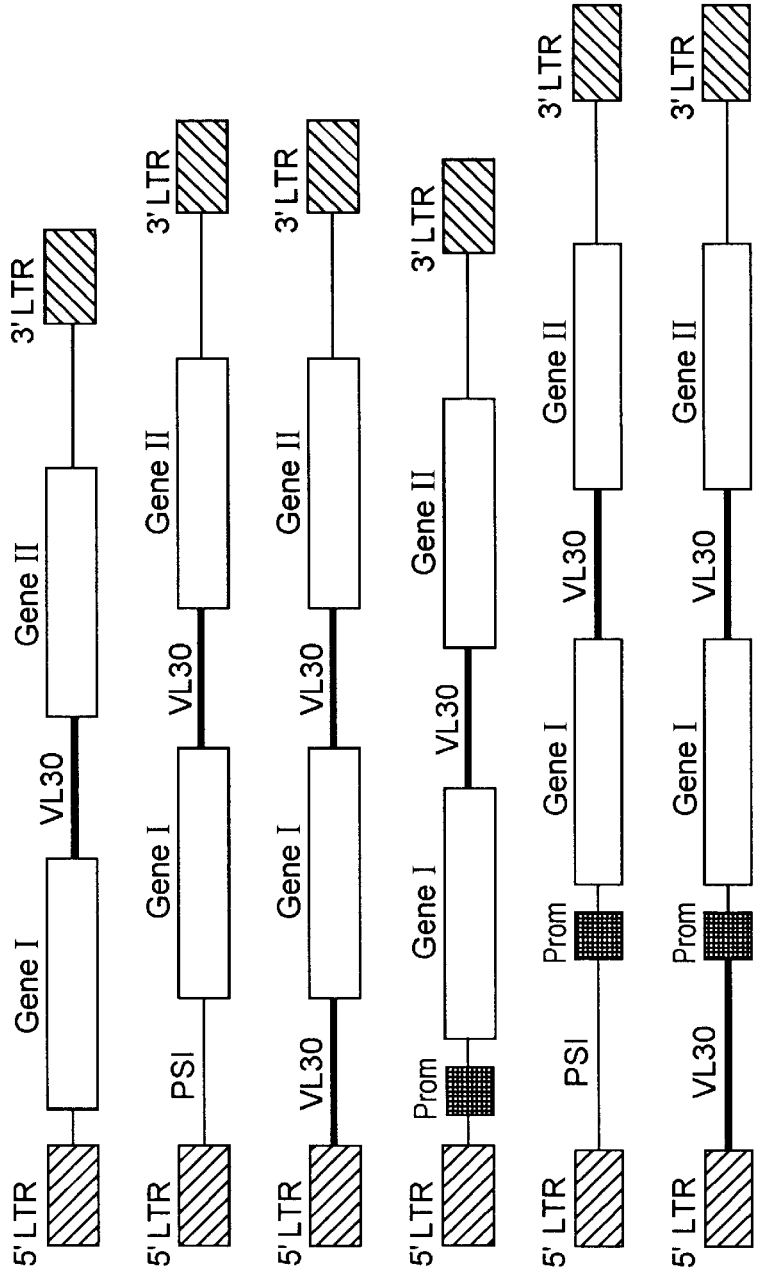

INTERNAL RIBOSOME ENTRY SITE, VECTOR CONTAINING IT AND THERAPEUTIC USE

This present application is a national phase application under 35 U.S.C. 371 of PCT/FR95/00894, filed Jul. 5, 1995, which claimed priority to French application 94 08300, filed Jul. 5, 1994.

BACKGROUND OF THE INVENTION

The present invention relates to a DNA fragment isolated from a retrotransposon and comprising an internal ribosome entry site (IRES). More especially, it relates to expression vectors containing this DNA fragment, and in particular to polycistronic vectors permitting the efficient and stable expression of several genes of interest under the control of the same promoter. The present invention finds advantageous application in the field of gene therapy vectors.

The feasibility of gene therapy applied to man no longer needs to be demonstrated, and this relates to many therapeutic applications such as genetic disorders, infectious diseases and cancer. Many documents of the prior art describe the means of implementing gene therapy, in particular by the use of viral vectors. Generally speaking, the vectors are obtained by deletion of at least a portion of the viral genes which are replaced by the genes of therapeutic interest. Such vectors may be propagated in a complementation line which supplies in trans the deleted viral functions, to generate a viral vector particle which is defective for replication but capable of infecting a host cell. To date, retroviral vectors are among the ones most often used, but vectors originating from adenoviruses, adeno-associated viruses, poxviruses and herpesviruses may also be mentioned. This type of vector, their organization and their mode of infection are widely described in the literature available to a person skilled in the art.

It can be advantageous to have at one's disposal more efficacious gene therapy vectors capable, in particular, of producing several proteins of interest efficiently. However, the presence of several promoters within the same vector very often manifests itself in a reduction or even a loss of expression over time. This is due to a well-known phenomenon of interference between promoter sequences. In this context, the publication of International Application WO93/03143 proposes a solution to this problem which consists in employing an internal ribosome entry site (IRES). It describes a dicistonic retroviral vector for the expression of two genes of interest placed under the control of the same promoter. The presence of a picornavirus IRES site between these genes permits the production of the expression product originating from the second gene of interest by internal initiation of the translation of the dicistronic MRNA.

Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103–1112) and the EMCV virus (encephalo-myocarditis virus (Jang et al., J. Virol., 1988, 62, 2636–2643).

SUMMARY OF THE INVENTION

A new internal ribosome entry site has now been found in type VL30 murine retrotransposons, and this site has been shown to improve the translation of the coding sequences placed after it.

The genome of eukaryotic cells comprises a number of mobile genetic elements called transposons, which have the capacity to move from one site of the genome to another chosen at random. At the present time, their function and biological significance is not known. Some of them, the retrotransposons, appear to be related to retroviral proviruses by their organization and their mode of transposition (via an intermediate RNA, reverse transcription and integration in the cell genome). The different murine retrotransposons identified to date include the VL30 elements. The murine genome comprises from 150 to 200 copies of this. They are approximately 6 kb in length and possess direct repeats at their ends which recall retroviral LTRs. They are defective for replication and do not contain coding sequences (translation stop codons in the different reading frames). These elements as such are described in the literature and their nucleotide sequence is known (Adams et al., 1988, Mol. Cell. Biol., 8, 2989–2998; Van Beveren, Coffin and Hughes 1984. Restriction analysis of two genomes and restriction maps of representative retroviral proviruses and cellular oncogenes p. 559–1209, ed: Weiss, Teich, Varmus and Coffin; RNA tumor viruses, 2nd ed. Cold Spring Harbor Laboratory). Moreover, they may be transmitted from one cell to another by encapsidation in the presence of a helper virus.

It was not obvious to identify an IRES sequence in the murine VL30 elements, since the latter lack sequences coding for proteins and do not display a striking sequence homology with the sites already described in the literature. Furthermore, relative to these latter, the IRES site of a murine VL30 is especially advantageous. In the first place, it permits a rate of reinitiation of translation which is efficient and stable in the long term, and on the other hand, and unexpectedly, it can also, in the context of a retroviral vector, discharge the functions of dimerization and encapsidation, and do so independently of its position in the vector. And lastly, as a result of its small homology with retroviral sequences, its use reduces considerably the risk of production of viruses which are competent for replication, an advantageous property in the context of gene therapy vectors intended for human use.

DETAILED DESCRIPTION OF THE PREFERRED EMBODIMENTS

Accordingly, the subject of the present invention is an isolated DNA fragment comprising an internal ribosome entry site (IRES) and/or an encapsidation sequence, characterized in that it is derived from a retrotransposon.

Isolated DNA fragment is understood to mean a DNA fragment isolated from its context, that is to say not combined with another retrotransposon sequence other than the one defined below. The term "retrotransposon" refers to a mobile cellular genetic element which displays retroviral type features, in particular by the existence of direct repeats at both of its ends. IRES denotes a sequence capable of promoting the entry of ribosomes into an RNA molecule independently of the cap, at an internal site of this RNA. An encapsidation sequence is a sequence involved in the process of encapsidation of retroviruses or retroviral vectors by promoting the dimerization of two copies of the retroviral genome and permitting encapsidation of the dimer in viral particles. The term "derived" refers to a structure having a retrotransposon origin, but which may have undergone a few modifications or have been obtained by chemical synthesis, or alternatively various elements comprising portions of retrotransposon, such as HaMSV virus.

According to a preferred embodiment, a DNA fragment according to the invention is capable of exerting an IRES function and an encapsidation function when it is introduced into a suitable retroviral vector.

In the context of the present invention, a DNA fragment according to the invention is isolated from the 5' end of a retrotransposon, and in particular from the region which directly follows the direct repeat located at its 5' end (5' LTR-like), and especially the transfer RNA binding site (PBS). It goes without saying that it may be isolated by any technique in use in the field of the art, for example by cloning using suitable probes, by PCR (polymerase chain reaction) or alternatively chemical synthesis. For the purposes of the present invention, it comprises at least 100 nucleotides of said region, advantageously at least 200 nucleotides, preferably at least 300 nucleotides, as a preference at least 400 nucleotides and as an absolute preference at least 550 nucleotides, counting the nucleotides outside the 5' direct repeat. However, naturally, it may extend beyond this in the 3' direction up to at most 0.88 to 1.5 kb.

According to an altogether preferred embodiment, a DNA fragment according to the invention is derived from a rodent VL30 element, preferably of murine and most especially of rat or mouse origin. As regards the first variant, according to which a DNA fragment is isolated from a rat VL30, it is most especially preferable to employ a DNA fragment having a sequence substantially homologous to the sequence presented in the sequence identifier SEQ ID NO: 1, beginning at nucleotide 1 and ending at nucleotide 590 or, optionally, beginning at nucleotide 176 and ending at nucleotide 590.

According to the second variant (DNA fragment isolated from a mouse VL30), use will preferably be made of a DNA fragment having a sequence substantially homologous to the sequence presented in the sequence identifier SEQ ID NO: 2, beginning at nucleotide 1 and ending at nucleotide 788.

The term substantially homologous refers to a degree of homology of greater than 70%, advantageously greater than 80%, preferably greater than 90% and as an absolute preference greater than 95%. Thus, a DNA fragment according to the invention can have a sequence slightly different from one of the sequences described in the sequence identifiers 1 and 2, provided, however, that the substitution, deletion or addition of one or more nucleotides does not affect its IRES function and/or the encapsidation function.

Generally speaking, a DNA fragment according to the invention is intended to be integrated (in either orientation) in a vector for the transfer and expression of one or more gene(s) of interest. The choice of such a vector is wide, and the techniques of cloning into the selected vector are within the capacity of a person skilled in the art. In accordance with the objectives pursued by the present invention, it is possible to envisage a plasmid vector or a vector derived from an animal virus, and especially from a poxvirus (canarypox or vaccinia virus), adenovirus, baculovirus, herpesvirus, adeno-associated virus or retrovirus. Such vectors are amply described in the literature. In particular, when an adenoviral vector is selected, it may originate from a human adenovirus, preferably an animal adenovirus, preferably canine or avian, or alternatively a hybrid between a variety of species. The general technology relating to adenoviruses is disclosed in Graham and Prevec (1991, Methods in Molecular Biology, Vol. 7, Gene transfer and Expression Protocols; Ed E. J. Murray, the human Press Inc., 109–118).

In the context of the present invention, a DNA fragment according to the invention is preferably positioned upstream of a gene of interest in order to improve the translation of the expression product for which the latter codes. It may be included in an expression cassette of the monocistronic type (for the expression of a gene of interest placed under the control of a promoter) or polycistronic type (for the expression of at least two genes of interest placed under the control of the same promoter). Such a cassette may contain several "IRES site-gene of interest" elements in tandem, at least one of the IRES sites of which consists of a DNA fragment according to the invention. It is most especially preferable to employ it in a dicistronic cassette into which it may be inserted either upstream of the first gene of interest or upstream of the second, the latter variant being the preferred one.

When a vector according to the invention comprises several expression cassettes, these may be inserted in either orientation with respect to one another: in the same orientation (promoter acting in the same direction) or in the reverse orientation (promoter acting in the opposite orientation).

In the case where a vector according to the invention comprises several DNA fragments according to the invention, it is preferable for them to originate from retrotransposons of different origins. According to this particular embodiment, it is preferable for one of the fragments to be derived from a rat VL30 and to have, in particular, a sequence substantially homologous to SEQ ID NO: 1, and for the other one to be derived from a mouse VL30 and to have, in particular, a sequence substantially homologous to SEQ ID NO: 2.

According to an altogether preferred embodiment, a vector according to the invention is derived from an retrovirus. As examples, there may be mentioned avian retroviruses such as the avian erythroblastosis virus (AEV), the avian leukemia virus (AVL), the avian sarcoma virus (ASV), the spleen necrosis virus (SNV) and the Rous sarcoma virus (RSV), bovine retroviruses, feline retroviruses, murine retroviruses such as the murine leukemia virus (MuLV), the Friend virus (F-MLV) and the murine sarcoma virus (MSV), and primate retroviruses.

Naturally, other retroviruses may be employed. However, it is most especially preferable to make use of the Moloney murine leukemia virus (MoMuLV). The many retroviral vectors derived from the latter which are described in the literature, in particular the vector N2 or one of its derivatives, may be used in the context of the present invention.

The retroviral vectors which can be envisaged for the purposes of the present invention are shown diagrammatically in FIG. 1 (*a, b* and *c*). Naturally, these examples are not limiting. For greater clarity, the retroviral 5' and 3' LTRs are represented by a hatched box, the murine (mouse and/or rat alike) VL30 sequences by a bold line, the internal promoter by a stippled box, the genes of interest by a clear box and lastly the retroviral encapsidation region (Psi) by a fine line. As illustrated, the retroviral 5' LTR may be used as promoter for the expression of one or more gene(s) of interest, but it is also possible to make use of an internal promoter. Moreover, a retroviral vector according to the invention can, optionally, contain a retroviral encapsidation region such as the MoMuLV Psi sequence. However, the presence of the latter is not essential, inasmuch as a DNA fragment according to the invention can also discharge this function irrespective of its position in the retroviral vector according to the invention (upstream of a gene of interest and/or downstream of the 5' LTR).

For the purposes of the present invention, a gene of interest in use in the invention may be obtained from a eukaryotic or prokaryotic organism or from a virus by any conventional technique. It is preferably capable of producing an expression product having a therapeutic effect, and this can be a product homologous to the host cell or alternatively heterologous. The term expression product denotes a protein or a fragment of the latter. In the context of the present invention, a gene of interest can code for (i) an intracellular product, (ii) a membrane product present at the surface of the host cell or (iii) a product secreted out of the host cell. It can hence comprise suitable additional elements such as, for example, a sequence coding for a secretion signal. These signals are known to a person skilled in the art.

In accordance with the objectives pursued by the present invention, a gene of interest may code for a protein corresponding to all or part of a native protein such as is found in nature. The protein in question may also be chimeric, for example originating from the fusion of polypeptide of various origins, or a mutant displaying improved and/or modified biological properties. Such a mutant may be obtained by traditional biological techniques, by substitution, deletion and/or addition of one or more amino acid residues.

It is most especially preferable to employ a gene of therapeutic interest coding for an expression product capable of inhibiting or delaying the establishment and/or development of a genetic or acquired disorder. A vector according to the invention is intended especially for the prevention or treatment of cystic fibrosis, hemophilia A or B, Duchenne or Becker type myopathy, cancer, AIDS and other bacteria or infectious diseases due to a pathogenic organism: virus, bacteria, parasite or prion. The genes of interest which can be used in the present invention are those which code for the following proteins:

a cytokine and in particular an interleukin, an interferon, a tissue necrosis factor and a growth factor, and in particular a hematopoietic growth factor (G-CSF, GM-CSF), a factor or cofactor involved in coagulation, and in particular factor VIII, factor IX, von Willebrand factor, antithrombin III, protein C, thrombin and hirudin, an enzyme, and in particular trypsin, a ribonuclease and β-galactosidase, an enzyme inhibitor such as $\alpha_1$-antitrypsin and the inhibitors of viral proteases an expression product of a suicide gene such as HSV virus (herpesvirus) type 1 thymidine kinase, an ion channel activator or inhibitor, a protein, the absence, modification or deregulation of expression of which is responsible for a genetic disorder, such as the CFTR protein, dystrophin or minidystrophin, insulin, ADA (adenosine diaminose), glucocerebrosidase and phenylhydroxylase, a protein capable of inhibiting the initiation or progression of cancers, such as an expression product of tumor suppressing genes (p53, Rb genes, etc.), a toxin, an antibody, an immunotoxin, a protein capable of stimulating an immune response, and a protein capable of inhibiting a viral infection or its development, for example an antigenic epitope of the virus in question, an antibody or an altered variant of a viral protein capable of competing with the native viral protein.

Moreover, a gene of interest in use in the present invention may also code for a selectable marker enabling the host cells transfected by a vector according to the invention to be selected or identified. There may be mentioned the neo (neomycin) gene conferring resistance to the antibiotic G418, the dhfr (dihydrofolate reductase) gene, the CAT (chloramphenicol acethyltransferase) gene or alternatively the gpt (xanthine phosphoribosyl) gene.

Generally speaking, for the expression of one or more gene(s) of interest, use will be made of a promoter which is functional in the host cell in question, and preferably a human cell. The choice of promoter is very wide and within the capacity of a person skilled in the art. It can be a promoter naturally governing the expression of a gene of interest in use in the present invention, or any other promoter (of eukaryotic or viral origin). Moreover, it can be ubiquitous in nature or regulable, in particular in response to certain tissue-specific or event-specific cellular signals. As a guide, it may be advantageous to employ a tissue-specific promoter when it is desired to target the expression of the gene or genes of interest in a particular cell or cell type, for example lymphocytes in the context of AIDS, lung cells in the context of cystic fibrosis or muscle cells in the context of myopathies.

As non-limiting examples, there may be mentioned, in particular, the SV40 (simian virus 40), HMG (hydroxymethylglutarylcoenzyme A) and TK (thymidine kinase) promoters, retroviral LTRs and especially that of MoMuLV or MSV when a retroviral vector is employed, the adenovirus type 2 MPL late promoter (major late promoter), in particular in the context of an adenoviral vector, the 7.5K and H5R promoters intended in particular for vectors derived from poxviruses, and most especially the vaccinia virus, the PGK (phosphoglycerate kinase) promoter, the liver-specific promoters of the genes coding for $\alpha_1$-antitrypsin, factor IX, albumin and transferrin, the promoters of the immunoglobulin genes which permit expression in lymphocytes, and lastly the promoters of the genes coding for the surfactant or the CFTR protein which display some degree of specificity for lung tissues.

Moreover, an expression cassette present in a vector according to the invention can contain other sequences needed for the expression of the gene or genes of interest, at both transcriptional and translational levels; for example transcription activating sequences of the enhancer type, introns, transcription termination signals and, as stated above, a secretion signal.

The invention also covers the viruses and viral particles obtained by transfection of the viral vector according to the invention into an appropriate complementation line. Depending on the type of viral vector used, a person skilled in the art knows the complementation lines which can be employed to generate infectious viral particles, as well as the method to be carried out. As regards an adenoviral vector, use may be made of the line 293 (Graham et al., 1977, J. Gen. Virol., 36, 59–72).

In the context of a retroviral vector according to the invention, it is possible to envisage employing ecotropic cell lines such as the CRE (Danos and Mulligan, 1988, Proc. Natl. Acad. Sci. USA. 85, 6460–6464) or GP+E-86 (Markowitz et al., 1988, J. Virol., 62, 1120–1124) line. However, it is most especially preferable to employ an amphotropic complementation line such as the PG13 (Miller et al., 1991, J. Virol., 65, 2220–2224) or Psi Env-am (Markowitz et al., 1988, T.A.A.P. Vol. CI, 212–218) line. Generally, the infectious viral particles are recovered in the culture supernatant of the complementation cells transfected with a retroviral vector according to the invention.

The invention also extends to eukaryotic cells comprising a DNA fragment according to the invention. They may be obtained by infection with infectious viral particles according to the invention, or by introduction of a plasmid or viral vector, either in vitro (in a cell removed from a patient or animal) or directly in vivo. The methods for introducing a vector into a cell are conventional. It is possible to employ the calcium phosphate precipitation technique, the DEAE-dextran technique, direct injection of the vector or of a portion of the latter into a cell or alternatively encapsulation in molecules of the liposome type. Moreover, the vectors according to the invention may be present in the host cell either in integrated form in the cell genome or in episomal form, either in the nucleus or in the cytoplasm of the cell. The cell according to the invention is advantageously a mammalian cell, and preferably a human cell.

The present invention also relates to the therapeutic use of a vector or a cell according to the invention, for the preparation of a pharmaceutical composition intended for the treatment and/or prevention of a genetic disorder or of an acquired disease such as cancer or an infectious disease. However, such a use is not limited to an application of the somatic gene therapy type. In particular, a vector according to the invention may be used for other purposes, such as the production by the recombinant method, in eukaryotic cells, of expression products intended for inclusion after purification in said pharmaceutical composition.

The invention is also directed towards a pharmaceutical composition comprising as therapeutic or prophylactic agent a vector or a cell according to the invention, in combination with a vehicle which is acceptable from a pharmaceutical standpoint.

A pharmaceutical composition according to the invention may be manufactured in a conventional manner. In particular, a therapeutically effective amount of such an agent is combined with an acceptable vehicle, diluent or adjuvant. It may be administered by any administration route, in a single dose or a dose repeated after a certain time interval. The amount to be administered will be chosen in accordance with various criteria, especially the use as treatment or as vaccine, the administration route, the patient, the type of disorder to be treated and the point to which it has progressed, the duration of the treatment, and the like. As a guide, a pharmaceutical composition according to the invention comprises between $10^4$ and $10^{14}$ pfu (plaque forming units), advantageously between $10^5$ and $10^{13}$ pfu and preferably between $10^6$ and $10^{11}$ pfu of viral particles.

Moreover, the invention relates to a method for the treatment of genetic disorders, cancers and infectious diseases, according to which a therapeutically effective amount of a vector or a cell according to the invention is administered to a patient requiring such a treatment. According to a first therapeutic protocol, they may be administered directly in vivo, for example by intravenous or intramuscular injection or by aerosolization in the lungs. Alternatively, an ex vivo gene therapy protocol may be adopted, which consists in removing the cells from a patient, stem cells of the bone marrow or peripheral blood lymphocytes, in transfecting them with a vector according to the invention and in culturing them in vivo before reimplanting them in the patient.

The invention also relates to an isolated DNA fragment containing an encapsidation sequence (Psi) derived from a Moloney murine leukemia virus (MoMuLV) as internal ribosome entry site (IRES), and to its use in the context of expression vectors such as those mentioned above, and especially retroviral vectors. The vector used will be polycistronic, and will preferably comprise two genes of interest under the control of the same promoter and will have an MoMuLV Psi sequence between the two genes. The vector may include additional genes of interest, either in the form of a polycistronic cassette (several "IRES-gene of interest" elements in tandem, at least one IRES of which consists of a Psi sequence derived from MoMuLV), or in the form of an independent cassette provided with its own promoter. Naturally, the invention also covers the viral particles and eukaryotic cells comprising such a vector, their therapeutic use and also a pharmaceutical composition. It may be noted that an IRES site according to the invention is preferably carried by the sequences extending from nucleotides 210 to 1035 of the MoMuLV genome (+1 representing the transcription initiation site).

The invention is illustrated below by reference to the figures which follow.

BRIEF DESCRIPTION OF THE DRAWINGS

FIGS. 1A, 1B and 1C show a few retroviral vectors which can be used in the context of the invention, 1A: of the monocistronic type, 1B: of the dicistronic type and 1C: of mixed type comprising mono- and dicistronic expression cassettes. The 5' and 3' LTRs are represented by a hatched box, the murine (rat or mouse) VL30 sequences by a bold line, the retroviral Psi sequence by a fine line, the internal promoter by a stippled box and lastly the genes of interest by a clear box.

EXAMPLES

Figure 1C:
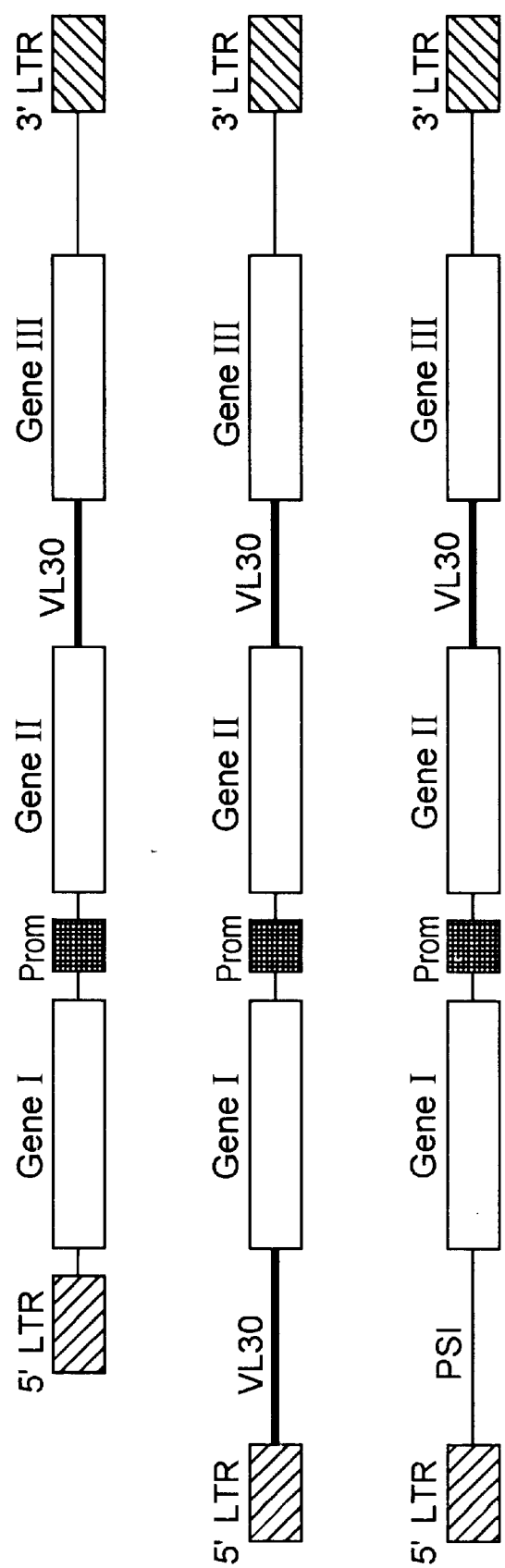

The constructions described below are carried out according to the general techniques of genetic engineering and molecular cloning detailed in Maniatis et al. (1989, Laboratory Manual, Cold Spring Harbor Laboratory Press, Cold Spring Harbor, N.Y.), or according to the manufacturer's recommendations when a commercial kit is used. The filling in of protruding 5' ends may be carried out using the Klenow fragment of E. coli DNA polymerase, and the destruction of protruding 3' ends in the presence of phage T4 DNA polymerase. The PCR techniques are known to a person skilled in the art and abundantly described in PCR Protocols, a guide to methods and applications (Ed: Innis, Gelfand, Sninsky and White, Academic Press, Inc.).

Moreover, the position of the rat and mouse VL30 sequences is indicated by reference to the RNA molecule, position+1 corresponding to the first nucleotide of the RNA molecule, that is to say to the transcription initiation site in the DNA molecule (first nucleotide of the R sequence). As regards the mouse VL30 sequences, the RNA positions 362–575 and 362–1149 correspond to the DNA positions 631–844 and 631–1418, respectively, of the sequence described in Adams et al. (1988, Mol. Cell. Biol., 8, 2989–2998)

EXAMPLE 1: Studies of in vitro expression

1. Construction of expression vectors

The vector pCB28 is obtained in the following manner:

The EcoRI-NheI fragment of PLNPOZ (Adam et al., 1991, J. Virol. 65, 4985–4990) is cloned into Bluescript II KS+ digested with EcoRI and SpeI to give pCB25. The HindIII-XbaI fragment of pCB25, containing the sequences coding for neomycin (neo), the poliovirus IRES site and the β-galactosidase gene (LacZ), is cloned into the vector pRc/

CMV (Invitrogen) from which positions 1284 to 3253 have been deleted and which has been digested with HindIII and XbaI. A fragment carrying the viral sequences of the F-MLV virus from positions 1 to 651 is generated by PCR using the primers 6 and 7 (SEQ ID NO: 3 and 4). A DNA preparation obtained from this virus by standard techniques may be used as template. The PCR fragment is digested with XhoI and BamHI and then inserted between the neo and LacZ genes of pCB27 partially digested with XhoI and BamHI.

A series of fragments carrying VL30 sequences of determined size, respectively:

from positions 1 to 794,
from positions 205 to 794, and
from positions 380 to 794, is then inserted between the neo and LacZ genes of pCB28 (also described in Berlioz and Darlix, 1995, J. Virol. 69, 2214–2222) linearized with NheI. The VL30 sequences were generated by PCR from the pVL-CG20 template (Torrent et al., 1994, J. Virol, 68, 661–667). It is within the capacity of a person skilled in the art to design suitable primers from the sequence data and provided, in addition, with an NheI site at their ends (in this connection, the oligonucleotides described in SEQ ID NO: 7 and 8 may be suitable for positions 205 to 794). pVL-D1-794, pVL-D205-794 and pVL-D380-794 are obtained, depending on the VL30 sequence inserted.

In all these vectors, the dicistronic cassette neo-VL30-LacZ is under the control of the T7 RNA polymerase promoter for in vitro expression, and of the cytomegalovirus (CMV) early promoter for expression in eukaryotic cells. It may be noted that the initiation AUG of the lacZ gene is placed in a favorable context for the initiation of translation according to Kozak's rule (A/GCCAUGG; Kozak, 1986, Cell 44, 283–292).

2. In vitro translation of dicistronic RNAs

Dicistronic RNAs are generated by in vitro synthesis from 5 μg of recombinant pVL plasmids linearized with XbaI. The transcription reaction proceeds for 3 h at 37° C. in 0.1 ml of 40 mM Tris-HCl (pH 7.5), 6 mM MgCl$_2$, 2 mM spermidine, 10 mM dithiothreitol, 10 mM NaCl, 0.5 mM each of the ribonucleoside triphosphates in the presence of 40 U of T7 RNA polymerase and 80 U of RNAsin (RNase inhibitor). After treatment with DNase (RQ1), the RNAs are extracted with phenol/chloroform and precipitated with ethanol. They are then redissolved in sterile double-distilled water and subjected to agarose gel electrophoresis to verify their integrity (single band migrating at the expected size of 4.6 to 5 kb, depending on the plasmid).

The dicistronic RNAs (10 μg of RNA/ml) are then translated in vitro in a rabbit reticulocyte lysate system (RRL system, Promega) at 50% of its original concentration in the presence of 1 mCi [$^{35}$S]methionine/ml (Amersham) (reaction time 1 h at 31° C.). The reaction mixture is supplemented with potassium acetate and potassium chloride to a final concentration of 60 mM and 40 mM, respectively.

The tubes are placed at 100° C. in 62.5 mM Tris-HCl (pH 6.8), 2% SDA, 10% glycerol, 5% β-mercaptoethanol and 0.02% bromophenol blue, and the $^{35}$S-labeled proteins are analyzed by electrophoresis on 10% polyacrylamide/0.2% SDS gel. Quantification of the translation products of the neo and LacZ genes is performed by scanning. The neo protein is used for standardization of the level of translation, and the amount of β-galactosidase synthesized (MW 110 kDa) is evaluated.

The RNAs produced from each of the vectors enable the expression products of the two genes (neo and β-galactosidase) to be synthesized, which indicates that they are dicistronic and suggests the existence of an IRES in the VL30 sequences employed, effecting the initiation of the translation of the second cistron resulting in the production of β-galactosidase.

When the reaction is examined quantitatively, the βgal/neo ratio is similar for the vectors pVL-D1-794 and pVL-D205-794. Hence the sequences 1–205 of VL30 seem to have little influence on the mechanism of initiation of translation. Advantageously with the vector pVL-D380-794, the level of synthesis of β-galactosidase is higher. These experiments suggest that the sequences 380 to 794 of the rat VL30 have the capacity to initiate the translation of a cistron on the 3' side via an internal ribosome entry mechanism.

EXAMPLE 2: Retroviral vectors comprising a sequence of a rat VL30

1. Construction of dicistronic vectors

The plasmid pCB71 is obtained in the following manner:

An EcoRI-XbaI fragment is isolated from the plasmid Cla12-AP and cloned between the same sites of Bluescript II KS+ (Stratagene) to generate pCB70. This fragment comprises the human alkaline phosphatase (AP) gene described in the prior art (Fekete and Cepko, 1993, Mol. Cell. Biol., 13, 2604–2613). The introduction of appropriate restriction sites is within the capacity of the person skilled in the art.

Concomitantly, the neomycin gene (neo; positions 4 to 844) is amplified by PCR from the vector pLNPOZ (Adam et al., 1991, supra) and using the primers 10 and 11 (SEQ ID NO: 5 and 6) equipped at their ends with SalI, SpeI and BamHI restriction sites. The PCR fragment generated is digested with SalI and BamHI, and introduced with the EcoRV-SalI fragment of pCB70 carrying the alkaline phosphatase gene into the vector pLNPOZ digested with BalI and BamHI.

A 0.59-kb DNA fragment containing the rat VL30 sequences (positions 205 to 794) and equipped at its 5' and 3' ends with an NheI site is isolated by PCR. Plasmid pVL-CG20 (Torrent et al., 1994, supra) is employed as template, and the oligonucleotides 12 and 13 recorded in SEQ ID NO: 7 and 8 are also employed. The PCR fragment is digested with NheI before being inserted into the vector pCB71 digested with SpeI, to give pCBT2. For purposes of information, a translation initiation ATG codon placed in a favorable Kozak context (A/GCCATGG), which will then enable a coding sequence lacking an initiation codon to be introduced, has been included in the oligonucleotide 13.

The final construction pCBT2 (FIG. 2) contains the MoMuLV 5' LTR, the human alkaline phosphatase gene and a 0.59-kb fragment isolated from rat VL30 (positions 205 to 794) followed by the neomycin gene and the MoMuLV 3' LTR.

The construction of the plasmid pCBT1 is performed in the following manner:

A DNA fragment containing the rat VL30 sequences (positions 205 to 379) is generated by PCR from the vector pVL-CG20 and the oligonucleotides 8 and 9 (SEQ ID NO: 9 and 10). After digestion with NheI, the fragment is inserted into the vector pCB28 also cleaved with NheI, to give pCB57. This NheI fragment is isolated from pCB57 and introduced into the vector pCB71 digested with SpeI. As above, the fragment contains a translation initiation codon placed in a Kozak context. pCBT1 (FIG. 2), which is identical to pCBT2 except for the length of the rat VL30 fragment (0.175 kb instead of 0.59 kb), is generated.

2. Construction of the monocistronic vector pVL-CT2

Figure 2:
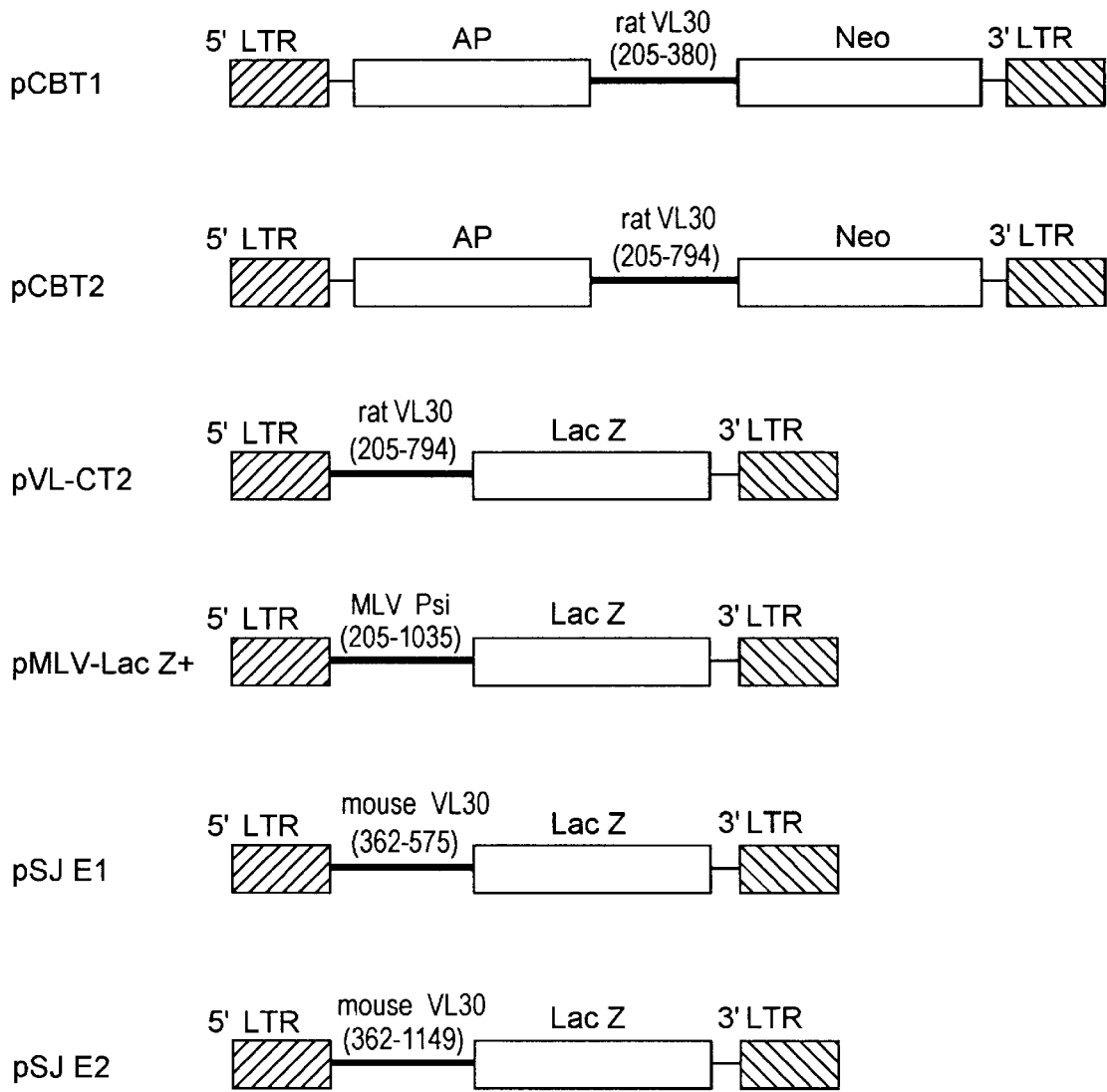
FIG. 2 shows diagrammatically the vectors pVLCT2, pCBT1, pCBT2, pMLV-LacZ+, pSJE1 and pSJE2.

A DNA fragment containing the HaMSV sequences (position+1 to +794), equipped at its 3' end with an NcoI site, is isolated by PCR. Plasmid pVL-CG20 (Torrent et al, 1994, supra) is employed as template, and the oligonucleotides 16 and 13 recorded in SEQ ID NO: 11 and 8 are also employed. The PCR fragment is digested with SmaI and NcoI before being inserted into the vector pLNPOZ (Adam et al., 1991, supra) digested with NcoI and partially with SmaI, to give pVL-CT2 (FIG. 2).

3. Generation of infectious viral particles and determination of the degree of encapsidation and the degree of expression of the neo, alkaline phosphatase and LacZ genes The ecotropic complementation line GP+E-86 (Markowitz et al., 1988, J. Virol., 62, 1120–1124) and the NIH3T3 target cells (mouse fibroblast cells) available at the ATCC are cultured at 37° C. in the presence of 5% $CO_2$ in DMEM medium (Dulbecco's Modified Eagle's Medium) supplemented with 5% of newborn calf serum. On the day before transfection and infection, the GP+E-86 cells and the NIH3T3 target cells are cultured on the basis of $5\times10^5$ cells per 10 cm dish and $1.5\times10^5$ cells per well, respectively. Viral infections are carried out according to the conventional protocol described in the literature. The titration method is the so-called limiting dilution point method.

The vectors pCBT1, pCBT2 and pVL-CT2, as well as the reference vector pMLV-LacZ (Torrent et al, 1994, supra), are transfected in parallel into GP+E-86 cells according to the method of Chen and Okyama (1987, Mol. Cell. Biol., 7, 2745–2753). The next day (D+1), the cells are washed according to the methods of the art and the culture supernatant is harvested on D+2. Different dilutions are used to infect the NIH3T3 target cells. The cells are cultured in selective medium (800 µg/ml of G418) for 24 hours after transfection or infection.

The expression of the LacZ gene is measured on an aliquot of culture of cells which are infected and transfected with pMLV-LacZ and pVL-CT2 after X-Gal staining. This staining technique is described in the standard works available to a person skilled in the art. It is also possible to use a commercial kit (Promega).

Similarly, the production of alkaline phosphatase in the transfected GP+E-86 cells and in the NIH3T3 cells infected with pCBT1 and pCBT2 is determined regularly over time. To this end, the cells are rinsed in PBS 1 buffer and fixed for 5 min at room temperature with a solution containing 2% of formaldehyde and 0.2% of glutaraldehyde in PBS×1. The cells were then rinsed twice in PBS×1 buffer and thereafter incubated for 30 min at 65° C. in PBS×1. They are washed in AP buffer (0.1M Tris-HCl pH 9.5, 0.1M NaCl, 50 mM $MgCl_2$). This buffer is then replaced by the staining solution (containing 0.1 mg/ml of 5-bromo-4-chloro-3-indolyl phosphate 1, 1 mg/ml of nito blue terazolium salt 1, 1 mM levamisol in AP buffer). The cells are incubated for 6 hours at room temperature protected from light. Stained cells correspond to phosphatase-positive cells.

The degree of encapsidation of each of the vectors is estimated by calculating the ratio of the number of stained infected cells (AP- or LacZ-positive) to the number of stained transfected cells (AP- or LacZ-positive) ×100. The results are shown in Table 1 below.

TABLE 1

| PLASMID | DEGREE OF ENCAPSIDATION |
|---|---|
| pMLV-LacZ+ | 100 |
| pVL-CT2 | 170 |
| pCBT1 | 1.8 |
| pCBT2 | 100 |

The data show that the DNA fragment of rat VL30 (positions 205 to 794) comprises an encapsidation signal which is at least as efficient as the Psi sequence of MoMuLV.

Surprisingly, the localization of the rat VL30 sequence between two genes has little effect on the efficiency of encapsidation of the retroviral genome (vector pCBT2 compared to pVL-CT2).

Moreover, when the expression of the AP and neo genes is monitored over time, the large majority of cells expressing the neo (G418 resistance) gene simultaneously express the phosphatase gene. The expression of both genes is stable over time, since more than 90% of G418-resistant cells are also phosphatase-positive after 40 days of culture in selective medium.

4. Analysis of RNAs

Cells at confluence are washed (PBS 1×) and then incubated for 1 hour at 37° C. in a lysis buffer (50 mM Tris-HCl pH 8.8; 0.3M NaCl; 0.5% SDS; 0.1% β-mercaptoethanol; 100 µg/ml proteinase K). The lysate is extracted twice with phenol. The nucleic acids are then precipitated in the presence of 2.5 volumes of cold ethanol. The DNA precipitate is recovered using a glass rod, while the RNAs are precipitated for 1 hour at −20° C. and then centrifuged for 30 minutes at 10,000 rpm at 4° C. The purified cellular RNA is taken up in 150 µl of sterile water.

The total cellular RNAs are incubated at 65° C. for 5 min in MOPS buffer (20 mM morpholinopropanesulfonic acid, 5 mM sodium acetate, 1 mM EDTA, pH 7) containing 6% formaldehyde, 50% formamide, 30% glycerol blue. The denatured RNAs are applied to 0.7% agarose gel under denaturing conditions (MOPS 1×, 6% formaldehyde). The RNAs are then transferred onto a nitrocellulose membrane in 25 mM sodium phosphate buffer for 1 hour 30 min at 800 mA. The membrane is exposed under UV (252 nm; 0.32 $J/cm^2$) to fix the RNAs. The membrane is then incubated for 4 hours at 42° C. in a prehybridization solution (50% formamide, 1M NaCl, 50 mM $NaPO_4$ pH 7, 10% dextran sulfate, 1% SDS, 250 µg/ml salmon sperm DNA denatured for 5 min at 100° C). The membrane is then hybridized for 14 hours at 42° C. in 50% formamide, 0.8M NaCl, 50 mM $NaPO_4$ pH 7, 10% dextran sulfate and 1% SDS. The neomycin probe used at an activity of $0.5\times10^9$ cpm/µg is denatured for 5 min at 100° C. and added to the hybridization solution. After hybridization, the membrane is washed in successive baths: 2×SSC, 1% SDS (2 times 10 min, room temperature), 2×SSC, 0.1% SDS (30 min, 65° C.) and 1×SSC, 0.1% SDS (30 min, 65° C.). The membrane is then dried and exposed at −80° C. for 72 hours.

The neomycin probe is complementary to the neomycin gene between positions 213 and 596, and corresponds to the PstI-NcoI fragment of pLNPOZ (Adam et al., 1991). The probe was labeled by primer extension with the Nonaprimer kit I kit (Appligene).

The cellular RNAs were extracted from GP+E-86 cells 72 hours after transfection with plasmid pCBT2, or alternatively from NIH3T3 cells infected with pCBT2 virions after 30 days of selection. Hybridization of these RNAs with a probe complementary to the neo gene reveals the presence of a single dicistronic RNA of identical size in the transfected and infected cells. Consequently, the simultaneous expression of the phosphatase and neomycin genes in 90–95% of the infected cells after 30 days of selection is due to the presence of a single dicistronic RNA.

5. Dicistronic retroviral vector containing two encapsidation signals.

Figure 3:
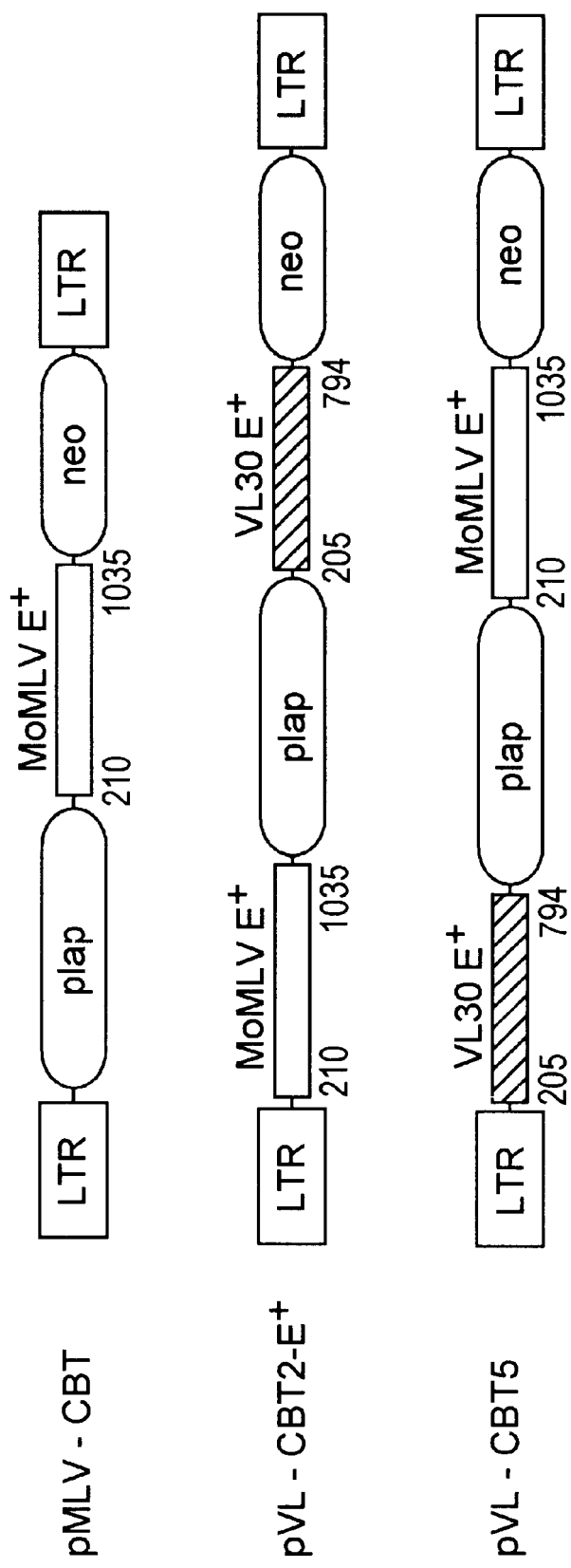
FIG. 3 shows diagrammatically the vectors PMLV-CBT, pVL-CBT2-E⁺and pVL-CBT5 (plap represents the alkaline phosphatase gene hereinafter designated AP).

This example describes the construction of dicistronic vectors containing one encapsidation signal in the normal position (downstream of the 5' LTR) and the second one between two cistrons. Two retroviral vectors are generated, (1) pVL-CBT2-E+ in which the MoMuLV signal is placed downstream of the 5' LTR and the rat VL30 sequence (205–794) between the genes coding for alkaline phosphatase and neo, and (2) pVL-CBT5 in which their respective positions are reversed.

pVL-CBT2-E+ results from the cloning of the EcoRI fragment isolated from pLNPOZ (Adam et al., 1991, supra) carrying the 5' LTR and encapsidation sequences of MoMuLV into pCBT2 previously digested with this same enzyme (FIG. 3).

pVL-CBT5 is obtained in the following manner: the sequences corresponding to the MoMuLV 5' LTR followed by the VL30 sequences (positions 205 to 794) are amplified by PCR from the pVL-CT2 template. It is within the capacity of a person skilled in the art to determine the primers which are suitable and to provide them with EcoRI sites at their 5' ends. The amplified fragment is digested with EcoRI and cloned into the vector pMLV-CTB (see below), also treated with EcoRI, to give pVL-CBT5 (FIG. 3).

6. Dicistronic retroviral vector containing the MoMuLV encapsidation signal in the central position.

The equivalent of pCBT2 is constructed, with the difference that the MoMuLV encapsidation signal (positions 210 to 1035) replaces that of rat VL30. It is isolated from the vector pLNPOZ by PCR using appropriate primers containing an NheI site at their ends. After NheI digestion, the amplified fragment is introduced between the AP and neo genes of pMLV-CB71 (Berlioz and Darlix, 1995, J. Virol. 69, 2214–2222) digested with SpeI. pMLV-CBT is obtained (FIG. 3).

7. Evaluation of the encapsidation functions and IRES of the vectors pMLV-CBT2-E+, pVL-CBT5 and pMLV-CBT The viral titers are determined transiently or stably according to the technology applied above, by evaluation of the number of cells expressing alkaline phosphatase. The results are shown in Table 2 below and compared with the dicistronic vector pCBT2.

TABLE 2

| Vector | Viral titers (AP+ cfu/ml) | |
|---|---|---|
| | Transient expression | Long-term expression |
| pCBT2 | $1 \times 10^4$ | $1 \times 10^5$ |
| pMLV-CBT | $2.5 \times 10^4$ | $2 \times 10^5$ |
| pVL-CBT2-E+ | $3 \times 10^4$ | $4 \times 10^5$ |
| pVL-CBT5 | $2.5 \times 10^4$ | $1.8 \times 10^5$ |

These data show that the presence of two encapsidation signals in a recombinant vector has no effect (pMLV-CBT compared to pVL-CBT5) or a moderate effect (pCBT2 compared to pVL-CBT2-E+) on the viral titer relative to a vector having only one signal. It is also observed that the position of these signals within the retroviral genome can influence their capacity for encapsidation (pVL-CBT2-E+ compared to pVL-CBT5), although to a small degree. In this connection, the combination "MoMuLV signal in the normal position and VL30 between the two cistrons" seems more efficient.

GP+E-86 cells are transfected with each of the retroviral vectors, and the levels of expression of the AP gene in the presence and absence of neomycin are evaluated. Neomycin-resistant and AP-positive cells are counted after 15 days of selection. The values obtained are slightly larger for the dicistronic vectors carrying both encapsidation signals than for their homologues carrying only one of them, which suggests that the presence of two encapsidation sequences, one of retroviral origin and the other from VL30, does not influence the gene expression of the cistrons. Moreover, in all cases, expression of the neo gene is efficient. In point of fact, this expression can be obtained only by internal initiation of the translation of the dicistronic RNAs mediated by the sequences preceding the neomycin cistron, namely VL30 (pCBT2 or pVL-CBT2-E+) or the encapsidation region of MoMuLV (PMLV-CBT and pVL-CBT5).

In conclusion, these experiments show that the VL30 and MoMuLV 5' sequences are both capable of promoting the encapsidation of a retroviral vector and the initiation of the translation of a cistron placed downstream.

EXAMPLE 3: Retroviral vector comprising an encapsidation sequence isolated from a mouse VL30.

1. Construction of vectors

A DNA fragment containing the mouse VL30 sequence (positions 362 to 1149) is amplified by PCR from the vector pKT403 (Adams et al, 1988, supra) and using the oligonucleotide primers 3 and 4 (SEQ ID NO: 12 and 13). The fragment generated is digested with BalI and NcoI before being inserted between the same sites of the vector pLNPOZ (Adam et al., 1991, supra). The vector pSJE2 is obtained.

Furthermore, a DNA fragment comprising a shorter sequence from mouse VL30 (positions 362–575), also obtained by PCR from the pKT403 template and the oligonucleotides 1 and 2 (SEQ ID NO: 14 and 15), is introduced into the vector pLNPOZ as described above. pSJE1 is obtained.

The vectors pSJE1 and pSJE2 comprise the MoMuLV 5' LTR, the mouse VL30 fragment mentioned, the LacZ gene and the MoMuLV 3' LTR. As a negative control, the vector pSJE3 is constructed, identical to the above two vectors but in which the VL30 sequences is replaced by a polylinker. It is obtained by introduction of the oligonucleotide 5 (SEQ ID NO: 16) between the BalI and NcoI sites of pLNPOZ.

2. Determination of the degree of encapsidation

The technology used is comparable to that described in Example 1. Briefly, the vectors PSJE1, 2 and 3 are transfected into murine complementation lines, GP+E-86 or CRIP (Danos and Mulligan, 1988, Proc. Natl. Acad. Sci. USA, 85, 6460–6464). The culture supernatant is used to infect the NIH3T3 murine target cells. The expression of the LacZ gene in the infected and transfected cells is measured after X-Gal staining. The viral titer corresponds to the ratio of the number of infected blue (LacZ+) cells to the degree of transfection multiplied by the volume of viral supernatant used. Table 3 below gives an estimation of the viral titers obtained for each of the pSJE vectors as a function of the starting complementation line. The vector pMLVLacZ+ (Torrent et al., 1994, supra) comprising the conventional encapsidation region of MoMuLV, is used as reference.

TABLE 3

| | TITERS ON GP + E86 (/ml) | | TITERS ON CRIP (/ml) |
|---|---|---|---|
| PLASMID | In transient expression | In long-term expression | In transient expression |
| pSJE1 | $0.1 \times 10^5$ | $0.3 \times 10^5$ | $0.7 \times 10^4$ |
| pSJE2 | $1 \times 10^5$ | $1.3 \times 10^5$ | $6.5 \times 10^4$ |
| pSJE3 | $<0.001 \times 10^5$ | $<0.001 \times 10^5$ | $<0.01 \times 10^4$ |
| pMLVlacZ+ | $0.85 \times 10^5$ | $2 \times 10^5$ | $7 \times 10^4$ |

The results show that the mouse VL30 sequence included between nucleotides 362 and 1149 comprises an encapsidation sequence which is at least as efficient as that of MoMuLV. A shorter VL30 sequence (positions 362–575) is still capable of encapsidation, though at a lower level. As expected, the vector pSJE3, lacking any encapsidation region, is incapable of generating viral particles.

Moreover, when the rat VL30 sequence is replaced in the vector pCBT2 by one of the mouse VL30 sequences (either the 0.78-kb fragment extending from positions 362 to 1149 or the 0.21-kb fragment extending from positions 362 to 575), an efficient degree of encapsidation and a correct expression of the alkaline phosphatase gene are measured.

We claim:

1. A polycistronic vector for the expression of at least two polynucleotide sequences comprising a promoter operably linked to a nucleotide sequence comprising elements encoding two or more proteins, and a DNA fragment of a VL30 retrotransposon comprising at least 100 bp to 1.5 kbp of a VL30 retrotransposon located between the elements of said nucleotide sequence, wherein said DNA fragment acts as an internal ribosome entry site.

2. A vector according to claim 1, wherein said VL30 retrotransposon is a murine VL30 retrotransposon.

3. A vector according to claim 1, wherein said VL30 retrotransposon is a rat VL30 retrotransposon.

4. A vector according to claim 3, wherein said rat VL30 retrotransposon has a nucleotide sequence consisting of SEQ ID NO: 1 beginning at nucleotide 1 and ending at nucleotide 590.

5. A vector according to claim 3, wherein said rat VL30 retrotransposon has a sequence consisting of SEQ ID NO: 1 beginning at nucleotide 176 and ending at nucleotide 590.

6. A vector according to claim 2, wherein said murine VL30 retrotransposon has a sequence consisting of SEQ ID NO: 2 beginning at nucleotide 1 and ending at nucleotide 788.

7. A vector according to claim 1, further comprising an encapsidation sequence.

8. A method of incorporating a DNA encoding a protein of interest into a cell in vitro comprising transforming said cell with a vector according to claim 1.

9. A polycistronic vector according to claim 1, wherein said vector is a plasmid vector or a viral vector from a virus selected from the group consisting of poxvirus, adenovirus, baculovirus, herpesvirus, adeno-associated virus, and retrovirus.

10. A polycistronic vector according to claim 1, wherein said vector is a retroviral vector further comprising an encapsidation sequence positioned downstream of the 5' LTR of said retroviral vector.

11. A polycistronic vector according to claim 10, wherein said encapsidation sequence is a retroviral encapsidation sequence.

12. An viral particle comprising a vector according to claim 10.

13. An isolated cell comprising a recombinant vector according to claim 1.

14. A composition comprising a recombinant vector according to claim 1.

15. A polycistronic vector for the expression of at least three polynucleotide sequence comprising a promoter operably to a nucleotide sequence comprising elements encoding three or more proteins, and DNA fragments of two or more different VL30 retrotransposons each comprising at least 100 bp to 1.5 kbp of a VL30 retrotransposons located between each of the elements of said nucleotide sequence, wherein said DNA fragments act as internal ribosome entry sites.

16. A vector according to claim 15, wherein a first DNA fragment comprises at least 100 bp to 1.5 kbp of a rat VL30 retrotransposon, and a second DNA fragment comprises at least 100 bp to 1.5 kbp of a mouse VL30 retrotransposon.

17. A vector according to claim 16, wherein said first DNA fragment has a nucleotide sequence selected from the group consisting of i) SEQ ID NO: 1 beginning at nucleotide 1 and ending at nucleotide 590 and ii) SEQ ID NO: 1 beginning at nucleotide 176 and ending at nucleotide 590; and said second DNA fragment has the nucleotide sequence of SEQ ID NO. 2 beginning at nucleotide 1 and ending at nucleotide 788.

18. A vector according to claim 15, comprising a gene coding for an expression product selected from the group consisting of factor VIII, factor IX, CFTR protein, dystrophin, insulin, gamma-interferon, an interleukin, and a selectable marker.

19. An isolated cell infected with a viral particle according to claim 12.

20. A composition comprising a viral particle according to claim 12.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Rattus
        (B) STRAIN: rat VL30 element (xi) SEQUENCE DESCRIPTION: SEQ ID NO:1:

```
GGCAAGCCGG CCGGCGTTTG TCTTGTCTGT TGTGTCTTGT CCTGTGAACG ATCGATCAAT      60

AGGCTCAGAT CTGGGGACTA TCTGGGCGGG CCAGAGAAGG AGCTGACGAG CTCGGACTTC     120

TCCCCCGCAG CCCTGGAAGA CGTTCCAAGG GTGGTTGGAG GAGAGGGAGA TGCGGATCCG     180

TGGCACCTCC GTCCGTTTTC GGAGGGATCC GCACCCTTGA TGACTCCGTC TGAATTTTTG     240

GTTTCAGTTT GGTACCGAAG CTGCGCGGCG CGCTGCTTGT TACTTGTTTG ACTGTTGGAA     300

TTGTTTGTCT TCTTTGTGAC CTGACTGTGG TTTTCTGGAC GTGTTGTGTC TGTTAGTGTC     360

TTTTTGACTT TTGTTTCGTG TTTGAATTTG GACTGACGAC TGTGTTTAAA ATCTTAGACC     420

GACGACTGTG TTTGAAATCA TGAAACTGTT TGCTTTGTTC GTCGAAGAGT TTTACTTGGT     480

CCCCTTAACG CTTAGTGAGT AAGAAACTTA ATTTTGTAGA CCCCGCTCTA GTGGCAGTGT     540

GTTGGTTGAT AGCCAAAGTT AATTTTTAAA ACATAGTGTT TTGGGGGTTG                590
```

(2) INFORMATION FOR SEQ ID NO:2:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: mouse VL30 element (xi) SEQUENCE DESCRIPTION: SEQ ID NO:2:

```
GATTCTTTGT TCTGTTTTGG TCTGATGTCT GTGTTCTGAT GTCTGTGTTC TGTTTCTAAG      60
```

-continued

```
TCTGGTGCGA TCGCAGTTTC AGTTTTGCGG ACGCTCAGTG AGACCGCGCT CCGAGAGGGA      120

GTGCGGGGTG GATAAGGATA GACGTGTCCA GGTGTCCACC GTCCGTTCGC CCTGGGAGAC      180

GTCCCAGGAG GAACAGGGGA GGATCAGGGA CGCCTGGTGG ACCCCTTTGA AGGCCAAGAG      240

ACCATTTGGG GTTGCGAGAT CGTGGGTTCG AGTCCCACCT CGTGCCCAGT TGCGAGATCG      300

TGGGTTCGAG TCCCACCTCG TGTTTTGTTG CGAGATCGTG GGTTCGAGTC CCACCTCGCG      360

TCTGGTCACG GGATCGTGGG TTCGAGTCCC ACCTCGTGTT TTGTTGCGAG ATCGTGGGTT      420

CGAGTCCCAC CTCGCGTCTG GTCACGGGAT CGTGGGTTCG AGTCCCACCT CGTGCAGAGG      480

GTCTCAATTG GCCGGCCTTA GAGAGGCCAT CTGATTCTTC TGGTTTCTCT TTTTGTCTTA      540

GTCTCGTGTC CGCTCTTGTT GTGACTACTG TTTTTCTAAA AATGGGACAA TCTGTGTCCA      600

CTCCCCTTTC TCTGACTCTG GTTCTGTCGC TTGGTAATTT TGTTTGTTTA CGTTTGTTTT      660

TGTGAGTCGT CTATGTTGTC TGTTACTATC TTGTTTTTGT TTGTGGTTTA CGGTTTCTGT      720

GTGTGTCTTG TGTGTCTCTT TGTGTTCAGA CTTGGACTGA TGACTGACGA CTGTTTTTAA      780

GTTATGCC                                                                788
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Murine leukemia virus
        (B) STRAIN: Friend strain (oligo 6)

(xi) SEQUENCE DESCRIPTION: SEQ ID NO:3:

```
GCTCGAGCTA GCTGCAGCGC CAGTCCTCCG                                        30
```

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Murine leukemia virus
        (B) STRAIN: Friend strain
        (C) INDIVIDUAL ISOLATE: oligo 7

(xi) SEQUENCE DESCRIPTION: SEQ ID NO:4:

```
CGGGATCCGC TAGCAAACTT AAGGGG                                            26
```

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: neomycin gene
        (C) INDIVIDUAL ISOLATE: oligo 10

(xi) SEQUENCE DESCRIPTION: SEQ ID NO:5:

GGGGTCGACA CTAGTGATTG AACAA                                                 25

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (B) STRAIN: neomycin gene
        (C) INDIVIDUAL ISOLATE: oligo 11

(xi) SEQUENCE DESCRIPTION: SEQ ID NO:6:

GCTCTAGAGG ATCCGGCAGG TTGGGCG                                               27

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: rat VL30 element
        (C) INDIVIDUAL ISOLATE: oligo 12

(xi) SEQUENCE DESCRIPTION: SEQ ID NO:7:

GGGCTAGCGG CAAGCCGGCC G                                                     21

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (B) STRAIN: rat VL30 element
        (C) INDIVIDUAL ISOLATE: oligo 13

(xi) SEQUENCE DESCRIPTION: SEQ ID NO:8:

GGGCTAGCCC CATGGCAACC CCCAAAACAC                                    30

(2) INFORMATION FOR SEQ ID NO:9:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: rat VL30 element
            (C) INDIVIDUAL ISOLATE: oligo 8

(xi) SEQUENCE DESCRIPTION: SEQ ID NO:9:

GGGCTAGCGG CAAGCCGGCC G                                             21

(2) INFORMATION FOR SEQ ID NO:10:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (B) STRAIN: rat VL30 element
            (C) INDIVIDUAL ISOLATE: oligo 9

(xi) SEQUENCE DESCRIPTION: SEQ ID NO:10:

GGGCTAGCCC CATGGCCGGA TCTCCCTC                                      28

(2) INFORMATION FOR SEQ ID NO:11:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Murine sarcoma virus
            (B) STRAIN: HaMSV
            (C) INDIVIDUAL ISOLATE: oligo 16

(xi) SEQUENCE DESCRIPTION: SEQ ID NO:11:

GCTCGAGCTA GCTGCAGCGC CAGTCCTCCG T                                  31

(2) INFORMATION FOR SEQ ID NO:12:

(i) SEQUENCE CHARACTERISTICS:
            (A) LENGTH: 28 base pairs

```
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: mouse VL30 element (oligo 3)

(xi) SEQUENCE DESCRIPTION: SEQ ID NO:12:

CCGAATTCTG GCCAGATTCT TTGTTCTG                                        28

(2) INFORMATION FOR SEQ ID NO:13:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (B) STRAIN: mouse VL30 element (oligo 4)

(xi) SEQUENCE DESCRIPTION: SEQ ID NO:13:

CCGCTAGCCC CATGGCAACT TAAAAACAG                                       29

(2) INFORMATION FOR SEQ ID NO:14:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: mouse VL30 element (xi) SEQUENCE DESCRIPTION: SEQ ID NO:14:

CCGAATTCTG GCCAGATTCT TTGTTCTG                                        28

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (B) STRAIN: mouse VL30 element (oligo 2)

(xi) SEQUENCE DESCRIPTION: SEQ ID NO:15:
```

```
CCGCTAGCCC CATGGCGTCC CTGATCC                                                   27

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: polylinker (oligo 5)

(xi) SEQUENCE DESCRIPTION: SEQ ID NO:16:

TGGCCAGCTG AAGCTTGCCA TGGG                                                      24
```